(12) United States Patent
Albee, Jr. et al.

(10) Patent No.: US 8,663,615 B2
(45) Date of Patent: Mar. 4, 2014

(54) BIO-POLYMER AIR EFFECTOR DELIVERY SYSTEMS

(76) Inventors: Paul Joseph Albee, Jr., Lambertville, PA (US); Eric Matthew Albee, Lambertville, NJ (US); Sandra Albee Keeley, Bensalem, PA (US)

( * ) Notice: Subject to any disclaimer, the term of this patent is extended or adjusted under 35 U.S.C. 154(b) by 0 days.

(21) Appl. No.: 13/211,358

(22) Filed: Aug. 17, 2011

(65) Prior Publication Data

US 2012/0308512 A1 Dec. 6, 2012

Related U.S. Application Data

(60) Provisional application No. 61/374,738, filed on Aug. 18, 2010.

(51) Int. Cl.
*A61L 9/00* (2006.01)
*A01N 35/00* (2006.01)

(52) U.S. Cl.
USPC .......................................... 424/76.1; 424/84

(58) Field of Classification Search
None
See application file for complete search history.

(56) References Cited

U.S. PATENT DOCUMENTS

| | | | |
|---|---|---|---|
| 4,071,616 A * | 1/1978 | Bloch | 424/76.4 |
| 2006/0008445 A1 * | 1/2006 | Garralda et al. | 424/84 |
| 2010/0166691 A1 * | 7/2010 | Pavlin | 424/64 |

* cited by examiner

*Primary Examiner* — Paul Dickinson
(74) *Attorney, Agent, or Firm* — Craig M. Bell

(57) ABSTRACT

The present invention comprises a bio-polymer based solid for the sustained release of an active agent into the air consisting of:
  a) a primary starched—based polymer;
  b) a secondary polyether block amide polymer, and:
  c) a filler component.
  d) one or more active oils The active oils can be one or more fragrances so as to provide an air freshening composition, a flavor to create a certain aromatic environment or a repellant such as insect repellants for the elimination of mosquitoes and the like. Animal repellants may be incorporated to ward off unwanted pets and wildlife outside the home and attractants may also be utilized in the production of fishing lures and the like.

11 Claims, No Drawings

BIO-POLYMER AIR EFFECTOR DELIVERY SYSTEMS

CROSS-REFERENCE TO RELATED APPLICATIONS

This application claims the benefit of priority of U.S. Provisional Appln. No. 61/374,738 filed on Aug. 16, 2010.

FIELD OF THE INVENTION

The present invention relates generally to solid compositions for the release of active agents into the air such as fragrances and insect repellants so as to provide more habitable surroundings.

BACKGROUND OF THE INVENTION

An aromatic sensory compound, which may be an odorant, aroma, fragrance or flavor, is a chemical compound that has a distinct smell or odor that may be sensed by the olfactory nervous system. A chemical compound has a smell or odor when two conditions are met: the compound needs to be volatile, so it can be transported to the olfactory system in the upper part of the nose, and it needs to be in a sufficiently high concentration to be able to interact with one or more of the olfactory receptors. Insect repellents are also aromatic compounds since insects such as mosquitoes intensely dislike the smell of chemical repellents such as DEET. In fact, a type of olfactory receptor neuron in special antennal sensilla of mosquitoes has been identified and is activated by them.

Fragrance oil(s), also known as aroma oils, aromatic oils, and flavor oils, are blended synthetic aroma compounds or natural essential oils that are diluted with a carrier such as propylene glycol, vegetable oil, or mineral oil. Aromatic oils are used in perfumery, cosmetics, flavoring of food, and in aromatherapy. To some people, synthetic fragrance oils are less desirable than plant-derived essential oils as components of perfume. An essential oil is a concentrated, hydrophobic liquid containing volatile aroma compound from plants. Essential oils are also known as volatile, ethereal oils or aetherolea, or simply as the "oil of" the plant from which they were extracted, such as oil of clove. An oil is "essential" in the sense that it carries a distinctive scent, or essence of the plant. Essential oils as a group do not need to have any specific chemical properties in common, beyond conveying characteristic fragrances.

Essential oils are generally extracted by distillation. Other processes include expression or solvent extraction. They are used in perfumes, cosmetics, soap and other products, for flavoring food and drink, and for scenting incense and household cleaning products. Fragrances useful in the practice of the practice of the present invention have been generally classified as Floral, Soft Floral, Floral Oriental, Oriental, Soft Oriental, Woody Oriental, Mossy Woods, Dry Woods, Citrus, Green and Water.

Various essential oils have been used medicinally at different periods in history. Medical application proposed by those who sell medicinal oils range from skin treatments to remedies for cancer, and are often based on historical use of these oils for these purposes. Such claims of use are now subject to regulation in most countries and as a result have grown more vague in order to stay within these regulations.

Interest in essential oils has revived in recent decades with the popularity of aromatherapy, a branch of alternative medicine which claims that the specific aromas carried by essential oils have curative effects. Oils are volatilized or diluted in a carrier oil and used for example, in massage, diffused in the air by a nebulizer, heated over a candle flame, or burned as incense.

U.S. Pat. No. 6,960,625 to Christensen et. al. discloses and claims a transparent polyurethane-hydrogel composition formulated as an air-freshener application that comprises the reaction product of a pre-polymer and a water-soluble crosslinker in an aqueous solvent with little to no organic solvent. The pre-polymer is present in an amount of no greater than about 5.0 wt. % based on the total weight of all the hydrogel components. The pre-polymer is generally prepared from at least one water-soluble polyol and an isocyanate. The transparent polyurethane-hydrogel composition allegedly has desirable gel physical properties and is useful for an air-freshener application.

U.S. Pat. No. 6,294,162 to Semoff et al. teaches a transparent gel air freshener and method for its' preparation. The gel composition comprises an aqueous gel, a fragrance, a surfactant and a co-solvent. The gel is transparent and free from visible particles and is homogeneous throughout. It has a uniform texture, a continuous structure, and includes volatile scented components. The gel is also capable of suspending solids such as botanicals therein for a decorative effect. The method provides for preparation of a gel air freshener, including the suspension of botanicals therein, while maintaining the clarity, texture, and structure of the gel. The method includes the steps of preparing a gel composition and cooling the gel composition. Botanicals may be added to the gel composition when it has gelled enough to support the botanical on the gel surface.

U.S. Pat. Nos. 7,166,259 to Beam et. al. and 5,695,692 to Kennedy are examples of commercially available plug-in or otherwise electric devices that automatically discharge a fragrance spray into a room for a given period of time.

SUMMARY OF THE INVENTION

The present invention comprises a bio-polymer based aromatic air scenting composition for the sustained release of an active agent into the air consisting of:
 a) a primary, starched-based thermoplastic compound;
 b) a secondary, polyether block amide thermoplastic elastomer;
 c) a filler component, and
 d) one or more active oils.

The active oils can be one or more fragrances so as to provide an air freshening composition, a flavor to create a certain aromatic environment or a repellant such as insect repellants for the elimination of mosquitoes and the like. Animal repellants may be incorporated to ward off unwanted pets and wildlife outside the home and attractants may also be utilized in the production of fishing lures, insect pheromones and the like.

DETAILED DESCRIPTION OF THE INVENTION

Bioplast 2189 is a starch based thermoplastic compound (BioTec GmBH) that is optimized for sheet extrusion, injection and compression molding. It is biodegradable and readily compostable in thin sections. This material is also useable in existing moulds and equipment and can be vividly colored. Made from corn starch that is mixed with other proprietary brand products for superior flexibility, Bioplast 2189 polymer is certified EN 13432 and DIN CERTCO biodegradable and compostable as well as EU & FDA (USA) Food Contact Approval. A bio-compostable material it is made from over 60% sustainable crop material and 20% non oil-based products such as poly-lactic acid.

Pebax® is a thermoplastic elastomer (Arkema Inc. King of Prussia, Pa.) which offers the widest range of performances (mechanical, chemical, processing) among the thermoplastic elastomers (TPE) wherein Pebax® stands for polyether block amide. Pebax® is plasticizer free and is a member of a chemically engineered polymer family. The Pebax® range enables one skilled in the art to bridge the gap between thermoplastics and rubbers. This secondary polymer enhances the fragrance holding power of the bio-polymer composition of the present invention. Polyether block amide (PEBA) is a thermoplastic elastomer (TPE) also known under the tradename of PEBAX. It is a block copolymer obtained by polycondensation of a carboxylic acid polyamide (PA6, PA11, PA12) with an alcohol termination polyether such as polytetramethylene glycol (PTMG), polyethylene glycol (PEG) and the like and mixtures thereof The general chemical structure is:

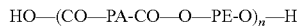

HO—(CO—PA-CO—O—PE-O)$_n$—H

Starch or amylum is a carbohydrate consisting of a large number of glucose units joined together by glycosidic bonds. This polysaccharide is produced by all green plants as an energy storage composition. It is the most important carbohydrate in the human diet and is contained in such staple foods as potatoes, wheat, maize (corn), rice, and cassava.

Pure starch is a white, tasteless and odorless powder that is insoluble in cold water or alcohol. It consists of two types of molecules: the linear and helical amylose and the branched amylopectin. Depending on the plant, starch generally contains 20 to 25% amylose and 75 to 80% amylopectin. Glycogen, the glucose storage unit of animals, is a more branched version of amylopectin.

Starch is processed to produce many of the sugars in processed foods. When dissolved in warm water, it can be used as a thickening, stiffening or gluing agent, giving wheat paste.

Starch molecules arrange themselves in the plant in semi-crystalline granules. Each plant species has a unique starch granular size: rice starch is relatively small (about 2 μm) while potato starches have larger granules (up to 100 μm). Although in absolute mass only about one quarter of the starch granules in plants consist of amylose, there are about 150 times more amylose molecules than amylopectin molecules. Amylose is a much smaller molecule than amylopectin.

Starch becomes soluble in water when heated. The granules swell and burst, the semi-crystalline structure is lost and the smaller amylose molecules start leaching out of the granule, forming a network that holds water and increases the mixture's viscosity. This process is called starch gelatinization. During cooking the starch becomes a paste and increases further in viscosity. During cooling or prolonged storage of the paste, the semi-crystalline structure partially recovers and the starch paste thickens, expelling water. This is mainly caused by the retro-gradation of the amylose. This process is responsible for the hardening, i.e., staling of bread, and for the water layer on top of a starch gel (syneresis).

Some cultivated plant varieties have pure amylopectin starch without amylose, known as waxy starches. The most used is waxy maize, others are glutinous rice and waxy potato starch. Waxy starches have less retrogradation, resulting in a more stable paste. High amylose starch, amylo-maize, is cultivated for the use of its gel strength.

The aromatic air scenting composition is formulated so that the primary starched-based thermoplastic compound comprises from about 10-90 wt % of the total weight of the bio-polymer composition. Preferably, the primary starched-based thermoplastic compound comprises from about 50-90 wt. % of the total weight of bio-polymer plastic. The secondary polyether block amide polymer of the device comprises from about 5.0-60 wt % of the total weight of bio-polymer compound, and preferably from about 20-40 wt. % of the total weight of bio-polymer plastic.

The active oil that gives off the "scent" to the environment that surrounds it such as those useful in the aromatic air scenting device of the present invention comprise active oils that are incorporated in the biopolymer plastic in amounts of from about 20.0-40.0 wt % of the total weight of bio-polymer plastic. Preferably the active oil that generates the aromatic scent is incorporated in an amount of from about 25.0-30.0 wt. % of the total weight of the device Fragrance oils useful in the practice of the present invention may be any one of the well known fragrances in the art and include citrus oil, cinnamon oil, mint oil, lavender oil, lilac oil, naval orange, blackberry sage, rose, pine, eucalyptus, and mixtures thereof. The fragrance oils useful in the practice of the present invention are well known in the art.

Flavoring agents or oils useful in the practice of the present invention include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture. Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication No. 1274, pages 63-258, by the National Academy of Sciences, may be used.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, mixtures thereof and the like.

The flavoring agent may be employed in either liquid form and/or dried form. When employed in the latter form, suitable drying means such as spray drying the oil may be used. Alternatively, the flavoring agent may be absorbed onto water soluble materials, such as cellulose, starch, sugar, maltodextrin, gum arabic and so forth or may be encapsulated. The actual techniques for preparing such dried forms are well known and do not constitute a part of this invention.

The flavoring agents of the present invention may be used in many distinct physical forms well known in the art to provide an initial burst of flavor and/or a prolonged sensation of flavor. Without being limited thereto, such physical forms include free forms, such as spray dried, powdered, and beaded forms, and encapsulated forms, and mixtures thereof.

Insect repellents useful in the practice of the present invention include eucalyptol, linalool, thujone and, in particular, N,N-Diethyl-meta-toluamide, abbreviated DEET This particular insect repellent is a slightly yellow oil and is the most common active ingredient in insect repellents. A slightly yellow liquid at room temperature, it can be prepared by converting m-toluic acid (3-methylbenzoic acid) to the corresponding acyl chloride, and reacting with diethylamine. DEET serves as a true repellent in that mosquitoes intensely dislike the smell of the chemical repellent.[6] A type of olfactory receptor neuron in special antenna sensilla of mosquitoes is activated by DEET and this neuron is known and has been identified. The olefactory receptors of insects that are sensitive to the other known insect repellents have also been identified. Moreover, in a behavioral test DEET had a strong repellent activity in the absence of body odor attractants such as 1-octen-3-ol, lactic acid, or carbon dioxide Other suitable insect repellants include d-cis/trans allethrin and other known repellents which are volatile or can be released into the air. Additional known natural insect repellents include, but are not limited to citronella, geraniol, natural geranium oil, catmint/catnip, and other natural and synthetic oils DEET is primarily intended to be applied to the skin or to clothing, and is primarily used to repel mosquitoes. In particular, DEET protects against tick bites, preventing several rickettsioses, tick-borne meningoencephalitis and other tick-borne diseases such as Lyme disease. It also protects against mosquito bites which can transmit dengue fever, West Nile virus, eastern equine encephalitis, and malaria. In addition to repellents for insects, repellents and attractants for other insects, mammals, reptiles, fish and others. These could include deer repellent or attractant, varmit repellent, ant repellent, and fish attractants for use in fishing lures and other such applications Suitable fish attractants useful in the practice of the present invention that can be molded into fishing lures and the like include, but are not limited to concentrated fish oils and pheromones., insect oils and pheromones, amphibian oils and pheromones, mollusk oils and pheromones, opine derivatives, inosine derivatives trimethylglycine derivatives, squid oil, menhaden oils, tuna oil, synthetic chemical attractants and mixtures thereof.

The following examples are provided to more specifically set forth and define the process of the present invention. It is recognized that changes may be made to the specific parameters and ranges disclosed herein and that there are a number of different ways known in the art to change the disclosed variables. And whereas it is understood that only the preferred embodiments of these elements are disclosed herein as set forth in the specification and drawings, the invention should not be so limited and should be construed in terms of the spirit and scope of the claims that follow herein.

The formulations of the present invention generally comprise a starch—based primary polymer such as BIOPLAST 2189®, a secondary polymer such as the polyether block amide (PEBAX-R®) and a filler selected from the group consisting of talc, mica, calcium carbonate, wood filler, bamboo, cellulose and cellulose derivatives, vegetable fiber and mixtures thereof. These are preferred fillers in the practice of the present invention but by all means the present invention should not be limited thereto. It was found that the solubility of the active ingredient such as the fragrance or insect repellant in the primary starch—based polymer by itself is limited. It was surprisingly discovered that the addition and incorporation of the secondary polyamide polymer greatly increases the solubility of the active compound while the filler compound appears to stabilize and modify the physical reactive properties of the compound.

EXAMPLE 1

Biopolymer compounds containing the active agent such as the fragrance or insect repellent of interest is formulated and then extruded using one a number of conventional single and twin compound extrusion mechanisms known in the art such as the Farrel Continuous Mixer (FCM), Banberry mixers and other extrusion processes commercially available and well known in the art. These generally comprise a pump that generates a uniform polymer melt temperature and pressure for the die. Generally, the extrusion compound process utilizes a 2.5 inch 24 to 1 simple screw extruder and melted polymer is fed to it from another extruder. Extrusion of the biopolymer active compounds were conducted through four (4) zones at varying temperatures as follows:

| Zone 1 | 300° F. | 300° F. | 300° F. |
| Zone 2 | 340° F. | 350° F. | 350° F. |
| Zone 3 | 360° F. | 370° F. | 370° F. |
| Zone 4 | 270° F. | 280° F. | 280° F. |
| RPM | 50 | 40 | 50 |
| AMPS | 5.0 | 4.0 | 3.5 |

The following compositions were prepared in the following ratios under the stated extrusion conditions.

| Sample No. | Formulation % Bioplast | % Pebax | Fragrance/Solvent | Wt % Increase |
|---|---|---|---|---|
| 1-1 | 100 | 0 | Benzyl Alcohol | 56.9 |
| 1-2 | 95 | 5 | | 88.2 |
| 1-3 | 90 | 10 | | 107.7 |
| 1-4 | 80 | 20 | | 130.8 |
| 1-5 | 60 | 40 | | 154.6 |
| 2-1 | 100 | 0 | Benzyl Benzoate | 21.8 |
| 2-2 | 95 | 5 | | 26.4 |
| 2-3 | 90 | 10 | | 31.3 |
| 2-4 | 80 | 20 | | 46.9 |
| 2-5 | 60 | 40 | | 154.6 |

| Sample No. | Formulation % Bioplast | % Pebax | Fragrance/Solvent | Wt % Increase |
|---|---|---|---|---|
| 3-1 | 100 | 0 | Citrus | 10.8 |
| 3-2 | 95 | 5 | | 14.9 |
| 3-3 | 90 | 10 | | 18.5 |
| 3-4 | 80 | 20 | | 32.4 |

-continued

| Sample No. | Formulation | | Fragrance/Solvent | Wt % Increase |
|---|---|---|---|---|
| | % Bioplast | % Pebax | | |
| 3-5 | 60 | 40 | | 69.5 |
| 4-1 | 100 | 0 | Apple Cinnamon | 16.2 |
| 4-2 | 95 | 5 | | 21.2 |
| 4-3 | 90 | 10 | | 26.1. |
| 4-4 | 80 | 20 | | 46.9 |
| 4-5 | 60 | 40 | | 80.3 |

| Sample No. | Formulation | | Fragrance/Solvent | Wt % Increase |
|---|---|---|---|---|
| | % Bioplast | % Pebax | | |
| 5-1 | 100 | 0 | Lavender | 21.0 |
| 5-2 | 95 | 5 | | 25.7 |
| 5-3 | 90 | 10 | | 33.5 |
| 5-4 | 80 | 20 | | 47.3 |
| 5-5 | 60 | 40 | | 86.5 |
| 6-1 | 100 | 0 | Blackberry Sage | 12.4 |
| 6.2 | 95 | 5 | | 18 |
| 6-3 | 90 | 10 | | 22.3 |
| 6-4 | 80 | 20 | | 35.3 |
| 6.5 | 60 | 40 | | 72.1 |
| 7-1 | 100 | 0 | Naval Orange | 11.8. |
| 7-2 | 95 | 5 | | 25.7 |
| 7-3 | 90 | 10 | | 33.5 |
| 7-4 | 80 | 20 | | 47.3 |
| 7-5 | 60 | 40 | | 86.5 |

As evidenced by the percentage weight increase of the respective samples, particularly those in which the percent Pebax reached levels of 40% or higher, considerably higher levels of the aromatic compounds such as benzyl benzoate, citrus, apple cinnamon and blackberry sage could be loaded into the bio-polymer starch carrier. The higher the load level of aromatic in the PEBaX, the greater the air freshening duration and strength.

EXAMPLE 2

Formulation (BLEND)
5% PEBAX—RNEW 35R53 (ARKEMA)
55% BIOME 106 (STARCH BASED COMPOUND—(BIOME BIOPLASTICS Ltd.)
20% FRAGRANCE OIL (ASPEN—MF153802)
10% WOOD FIBER (PINE 10020—AMERICAN WOOD FIBERS)

The blend was extruded (PELLETIZED) using a one (1) inch single screw extruder with a two (2) hole pelletizing die. The temperatures were as follows.

| ZONE 1 | 250° F. |
| ZONE 2 | 280° F. |
| ZONE 3 | 310° F. |
| ZONE 4 | 240° F. |
| SCREW SPEED (RPM) | 40 |

The pelletized compound was injection molded into three (3) inch diameter discs 0.125 inches thick using a BOY MODLE-55 injection molding unit. The melt temperature during molding was 280° F. the injection pressure was 800 p.s.i. The discs were then measured for a fragrance weight loss evaluation study as reported below to determine the rate of fragrance release from the compound.

The fragrance weight loss evaluation was carried out at room temperature (23° C.)

TABLE 1

| DAYS TESTED | FRAGRANCE LOSS % |
|---|---|
| 7 | 22.0% |
| 14 | 30.0% |
| 21 | 45.0% |
| 28 | 53.0% |
| 35 | 66.0% |

EXAMPLE 3

Formulation:
(Blend)
15% PLA—4240D (NATURE WORKS)
10% PEBAX 1205 (ARKEMA)
50% BIOPLAST GS 2189 (STARCH BASED COMPOUND—BIOTEC GmBh.)
15% FRAGRANCE OIL (ORCHID—5169421)
10% WOOD FIBER (PINE 10020—AMERICAN WOOD FIBERS)

The blend was extruded (pelletized) using a twenty-eight (28) mm twin screw extruder which was set up with a two hole pelletizing die. The temperatures were as follows.

| ZONE 1 | 240° F. |
| ZONE 2 | 240° F. |
| ZONE 3 | 250° F. |
| ZONE 4 | 280° F. |
| ZONE 5 | 280° F. |
| ZONE 6 | 280° F. |
| ZONE 7 | 270° F. |
| ZONE 8 | 260° F. |
| DIE | 240° F. |
| SCREW SPEED (RPM) | 150 |

Again the pelletized compound was injection molded into three (3) inch diameter discs 0.125 inches thick using a BOY MODLE-55 injection molding unit. The melt temperature during molding was 280° F. The injection pressure was 800 p.s.i. The discs were then measured for a fragrance weight loss evaluation study as reported below to determine the rate of fragrance release from the compound.

The fragrance weight loss evaluation was carried out at room temperature (23° C.). The results can be seen in Table 2

TABLE 2

| DAYS TESTED | % FRAGRANCE LOSS |
|---|---|
| 7 | 18 |
| 14 | 30 |
| 21 | 42 |
| 28 | 52 |
| 35 | 63 |

Again the pelletized compound was injection molded into three (3) inch diameter discs 0.125 inches thick using a BOY MODLE-55 injection molding unit. The melt temperature during molding was 280° F. The injection pressure was 800 p.s.i. The discs were then measured for a fragrance weight loss evaluation study as reported below to determine the rate of fragrance release from the compound.

EXAMPLE 4

Formulation:
(Blend)
10% PEBAX—1205 (MADE BY ARKEMA)
57% BIOPLAST GS 21879 (STARCH BASED COMPOUND—MADE BY BIOTEC Gmbh.)
20% FRAGRANCE OIL (LAVENDER)
5% BENZYL ALCOHOL
8% BAMBO FIBER (100 MESH)

The blend was extruded (pelletized) using a one (1) inch single screw extruder with a two (2) hole pelletizing die. The temperatures were as follows.

| | |
|---|---|
| ZONE 1 | 250° F. |
| ZONE 2 | 280° F. |
| ZONE 3 | 310° F. |
| ZONE 4 | 240° F. |
| SCREW SPEED (RPM) | 50 |

The pelletized compounds were extruded the pelletized compound was injection molded into three (3) inch diameter discs 0.125 inches thick using a BOY MODLE-55 injection molding unit. The melt temperature during molding was 280° F. The injection pressure was 800 p.s.i. The discs were then measured for a fragrance weight loss evaluation study as reported below to determine the rate of fragrance release from the compound.

The rods were then used for the determination of fragrance release though a weight loss as set forth above for a fragrance weight loss evaluation study to determine the rate of fragrance release from the compound. The fragrance weight loss evaluation was carried out at room temperature (23° C.)

TABLE 3

| DAYS TESTED | % FRAGRANCE LOSS |
|---|---|
| 1 | 6.6 |
| 4 | 10.8 |
| 7 | 21.7 |
| 14 | 24.3 |
| 21 | 27.6 |
| 30 | 43.3 |

As can be seen in the data from Examples 2-4, as evidenced by the percentage of fragrance oil weight loss in the respective samples over the course of a month, there is a dramatic decrease in the amount of fragrance oil retained by the samples over time, indicative of the release of fragrance oil and hence fragrance to the surrounding atmosphere over time goes on. Clearly the aromatic compounds such as benzyl benzoate, citrus, apple cinnamon and blackberry sage, that are loaded into the bio-polymer starch carrier during the preparation of the bio-polymer air effector delivery systems of the present inventions result in greater air freshening duration and strength.

What is claimed is:

1. An aromatic air scenting composition comprising a bio-polymer based fragranced plastic consisting of:
    a) a primary starched—based thermoplastic compound comprising from about 50-90 wt % of the total weight of the bio-polymer plastic;
    b) a secondary polyether block amide thermoplastic elastomer that comprises from about 20-40 wt. % of the total weight of the bio-polymer plastic;
    c) a filler component and;
    d) one or more active essential oils in an amount of from about 20-40 wt % of the total weight of bio-polymer plastic.

2. The aromatic composition of claim 1 wherein the primary starched based thermoplastic compound is selected from the group consisting of corn starch, potato starch, wheat starch, rice starch and mixtures thereof.

3. The aromatic composition of claim 2 wherein the secondary polyether block co-polymer is a thermoplastic elastomer obtained by the poly-condensation of a carboxylic acid polyamide with an alcohol termination polyether selected from the group consisting of polytetramethylene glycol (PTMG), polyethylene glycol (PEG) and mixtures thereof.

4. The aromatic air scenting composition of claim 3 wherein said active oil is selected from the group consisting of fragrance oils, flavor oils, insect repellents, animal repellants and animal attractants.

5. The aromatic composition of claim 4 wherein said fragrance oil is selected from the group consisting of floral, soft floral, floral oriental, oriental, soft oriental, woody oriental, mossy woods, dry woods, methyl salicylate, and citrene essential oils.

6. The aromatic composition of claim 4 wherein said fragrance oil is selected from the group consisting of citrus oil, cinnamon oil, mint oil, lavender oil, lilac oil, naval orange, blackberry sage.

7. The aromatic composition of claim 4 wherein said fragrance oil is a flavor oil selected from the group consisting of natural and artificial flavors, natural and synthetic fruit flavors, synthetic flavor oils and flavoring aromatics and/or oils, oleoresins and extracts derived from plants, leaves, flowers, fruits, and combinations thereof.

8. The aromatic composition of claim 4 wherein said fragrance oil is an insect repellent selected from the group consisting of DEET, eucalyptol, linalool, thujone, d-cis/trans allethrin citronella, geraniol, natural geranium oil, catmint/catnip, and other natural and synthetic oils and other known volatile repellents and mixtures thereof.

9. The aromatic composition of claim 8 wherein said flavor oil is selected from the group consisting of spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, cassia oil, vanilla, and citrus oils including lemon, orange, lime, grapefruit, and fruit essences including apple, pear, peach, grape, strawberry, raspberry, cherry, plum, pineapple, apricot and mixtures thereof.

10. The aromatic composition of claim 9 wherein said active oil is selected from the group consisting of an animal attractant and molded in the shape of a fishing lure.

11. The aromatic composition of claim 10 wherein said animal attractant molded in the shape of a fishing lure is selected from the group consisting of concentrated fish oils and pheromones, insect oils and pheromones, amphibian oils and pheromones, mollusk oils and pheromones, opine derivatives, inosine derivatives, tri-methylglycine derivatives, squid oil, menhaden oils, tuna oil and synthetic chemical attractants.

* * * * *